US00PP22622P2

(12) United States Plant Patent
Klemm et al.

(10) Patent No.: US PP22,622 P2
(45) Date of Patent: Apr. 3, 2012

(54) POINSETTIA PLANT NAMED 'NPCW10167'

(50) Latin Name: ***Euphorbia pulcherrima* Willd. ex Klotzsch**
Varietal Denomination: NPCW10167

(75) Inventors: Nils Klemm, Stuttgart (DE); Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/925,817

(22) Filed: Oct. 29, 2010

(51) Int. Cl.
*A01H 5/00* (2006.01)

(52) U.S. Cl. ..... Plt./307

(58) Field of Classification Search ..... Plt./307
See application file for complete search history.

*Primary Examiner* — Kent L Bell
(74) *Attorney, Agent, or Firm* — Jondle & Associates, P.C.

(57) ABSTRACT

A new poinsettia plant particularly distinguished by its strong stems, large bracts, and brilliant bright red color is disclosed.

1 Drawing Sheet

Genus and species: *Euphorbia pulcherrima* Willd. ex Klotzsch.

Variety denomination: 'NPCW10167'.

BACKGROUND OF THE NEW PLANT

The present invention comprises a new and distinct variety of poinsettia plant, botanically known as *Euphorbia pulcherrima* Willd. ex Klotzsch and hereinafter referred to by the variety name 'NPCW10167'. The new variety is the result of cross conducted between November 2004 to January 2005 in Kenya, district of Nairobi, between the female parent poinsettia plant 'P 359' (unpatented) and the male poinsettia plant 'Christmas Star' (U.S. Plant Pat. No. 16,870). A single plant selection was subsequently chosen for further evaluation and asexual propagation.

'NPCW10167' was first propagated via vegetative cuttings in Stuttgart, Germany in 2006 and has been asexually reproduced by vegetative cuttings in Stuttgart, Germany for over twelve generations. 'NPCW10167' has been found to retain its distinctive characteristics through successive asexual propagations via vegetative cuttings.

Plant Breeder's Rights for this variety were applied for in Canada on Jan. 25, 2010. 'NPCW10167' has not been sold or made publicly available more than one year prior to the filing date of this application.

SUMMARY OF THE INVENTION

The following are the most outstanding and distinguishing characteristics of this new variety when grown under normal horticultural practices in Stuttgart, Germany.

1. Strong stems;
2. Large bracts; and
3. Brilliant bright red color.

DESCRIPTION OF THE PHOTOGRAPH

This new poinsettia plant is illustrated by the accompanying; the colors shown are as true as can be reasonably obtained by conventional photographic procedures. The photograph is of a whole plant about four-months-old and in full flower.

DESCRIPTION OF THE NEW VARIETY

The following detailed description sets forth the distinctive characteristics of 'NPCW10167'. The data which define these characteristics were collected from asexual reproductions carried out in Stuttgart, Germany. The plant history was taken on four month-old plants grown in 13 cm pots from August to December 2009 with a minimum pinch date of 32 weeks. The plants were grown in a greenhouse covered with glass. Color readings were taken under natural light in the greenhouse. Color references are primarily to the R.H.S. Colour Chart of The Royal Horticultural Society of London (R.H.S.) ($5^{th}$ edition 2007).

DETAILED BOTANICAL DESCRIPTION OF THE NEW PLANT

Classification:
- *Family*.—Euphorbiaceae.
- *Botanical*.—*E. pulcherrima* Willd. ex Klotzsch.
- *Common*.—Poinsettia.

Parentage:
- *Female parent*.—'P 359' (unpatented).
- *Male parent*.—'Christmas Star' (U.S. Plant Pat. No. 16,870).

Growth:
- *Time to produce a rooted cutting*.—3 to 4 weeks.
- *Blooming habit*.—Intermittent; blooms from end of November to January.
- *Flowering response time*.—Approximately 52 days from beginning of short days until flowering.
- *Keeping quality*.—Excellent.

Plant:
- *Form*.—Triangular.
- *Growth habit*.—Upright.
- *Height*.—20.0 cm to 25.0 cm.
- *Width*.—20.0 cm to 30.0 cm.
- *Number of branches*.—5 to 7.
- *Average number of inflorescences per plant*.—5 to 7.

Stems:

*Color*.—Lower part: RHS 135C. Upper part: RHS 142B.

*Length*.—About 25.0 cm.

*Internode length*.—2.0 cm to 4.0 cm.

*Diameter*.—0.5 cm to 1.0 cm.

Leaves:

*Quantity*.—6 to 10 per lateral branch.

*Arrangement*.—Alternate.

*Shape*.—Ovate.

*Apex*.—Acute.

*Base*.—Truncate.

*Margin*.—Serrate.

*Lobes*.—Very few. Lobation characteristics: Shallow.

*Texture* (*both surfaces*).—Smooth.

*Vein color* (*both surfaces*).—RHS 135D.

*Variegation*.—Absent.

*Size*.—Length: 7.0 cm to 13.0 cm. Width: 4.0 to 9.0 cm.

*Color*.—Mature foliage: Upper surface: RHS 136A. Lower surface: RHS N 138B. Immature foliage: Upper surface: RHS 143B. Lower surface: RHS 143C.

*Leaf petiole*.—Length: 3.0 cm to 6.0 cm. Diameter: 0.2 cm to 0.3 cm. Color (both surfaces): RHS 47A.

Inflorescence:

*Type and habit*.—Compound corymbs of cyathia with colored flower bracts subtending the cyathia; inflorescence positioned above the foliage.

*Lastingness of inflorescence on the plant*.—4 to 5 weeks.

*Diameter*.—20.0 cm to 25.0 cm.

*Height*.—3.0 to 4.0 cm.

*Fragrance*.—Absent.

Bracts:

*Number of bracts per inflorescence*.—7 to 10.

*Shape*.—Ovate.

*Apex*.—Acuminate.

*Base*.—Rounded.

*Margin*.—Few shallow lobes.

*Size*.—Length: 10.0 cm to 15.0 cm. Width: 5.0 cm to 8.0 cm.

*Texture* (*both surfaces*).—Smooth.

*Venation pattern*.—Reticulate.

*Vein color*.—Upper surface: RHS 46A. Lower surface: RHS 47A.

*Bract color*.—Upper surface: RHS 46B. Lower surface: RHS 46C.

*Bract petiole*.—Length: 2.0 cm to 4.0 cm. Diameter: 0.2 cm. Color: Upper surface: RHS 53A. Lower surface: RHS 135D.

Cyme:

*Diameter*.—1.5 cm to 2.5 cm.

*Cyathia number*.—5 to 8 per inflorescence.

*Cyathium*.—Shape: Ovate. Diameter: 0.3 cm to 0.5 cm. Length: 0.4 cm to 0.7 cm. Color: RHS 135C and RHS 142B.

*Peduncle*.—Color: RHS 142B. Length: 0.1 cm to 0.2 cm. Diameter: 0.1 cm. Texture: Smooth.

*Nectar cups*.—Shape: Elongated and bent. Number: 1 per cyathium. Diameter: 0.1 cm when closed, 0.2 cm when open. Length: 0.3 cm to 0.5 cm. Color: RHS 142C when closed, RHS 13B when open.

Reproductive organs:

*Stamens*.—Quantity: 10 to 15 per cyathium. Anther: Shape: Ovate. Length: 0.05 cm. Color: RHS 12A. Filament: Length: 0.3 cm. Color: RHS 39A. Pollen: Quantity: Moderate. Color: RHS 6A.

*Gynoecium*.—Present.

*Pistil quantity per cyathium*.—1.

*Pistil length*.—0.2 cm. Stigma: Shape: Divided in two parts. Color: RHS 183A. Style: Length: Approximately 0.2 cm. Style color: RHS 183A. Ovary: Length: 0.05 cm. Color: RHS 143C.

Fruit and seed set: No fruit or seed have been observed.

Disease and insect/pest resistance: Good.

COMPARISON WITH PARENTAL AND COMMERCIAL VARIETYS

'NPCW10167' differs from the female parental poinsettia plant 'P 359' (unpatented) by having dark foliage while 'P 359' has light green foliage. Additionally, 'NPCW10187' has bright red bracts while 'P 359' has orange-red bracts.

'NPCW10167' differs from the male parent 'Christmas Star' (U.S. Plant Pat. No. 16,870) by having larger, bright red bracts, while 'Christmas Star' has smaller, dark red bracts.

'NPCW10167' differs from the commercial variety 'Cortez' (U.S. Plant Pat. No. 9,364) by having stronger stems and a brighter bract color, while 'Cortez' has weaker stems and a darker bract color. Additionally, the bracts of 'NPCW10167' are arranged at an acute angle, while 'Cortez' has flat bracts.

'NPCW10167' differs from its sibling, 'NPCW10164' (U.S. Plant patent application Ser. No. 12/925,805) by having bright red colored bracts (RHS 46B and RHS 46C), whereas 'NPCW10164' has dark red colored bracts (RHS 46A and RHS 47A). Additionally, 'NPCW10167' has ovate shaped bracts that are more elongated, whereas 'NPCW10164' has ovate shaped bracts that are more broad.

We claim:

1. A new and distinct variety of Poinsettia plant named 'NPCW10167' as described and shown herein.

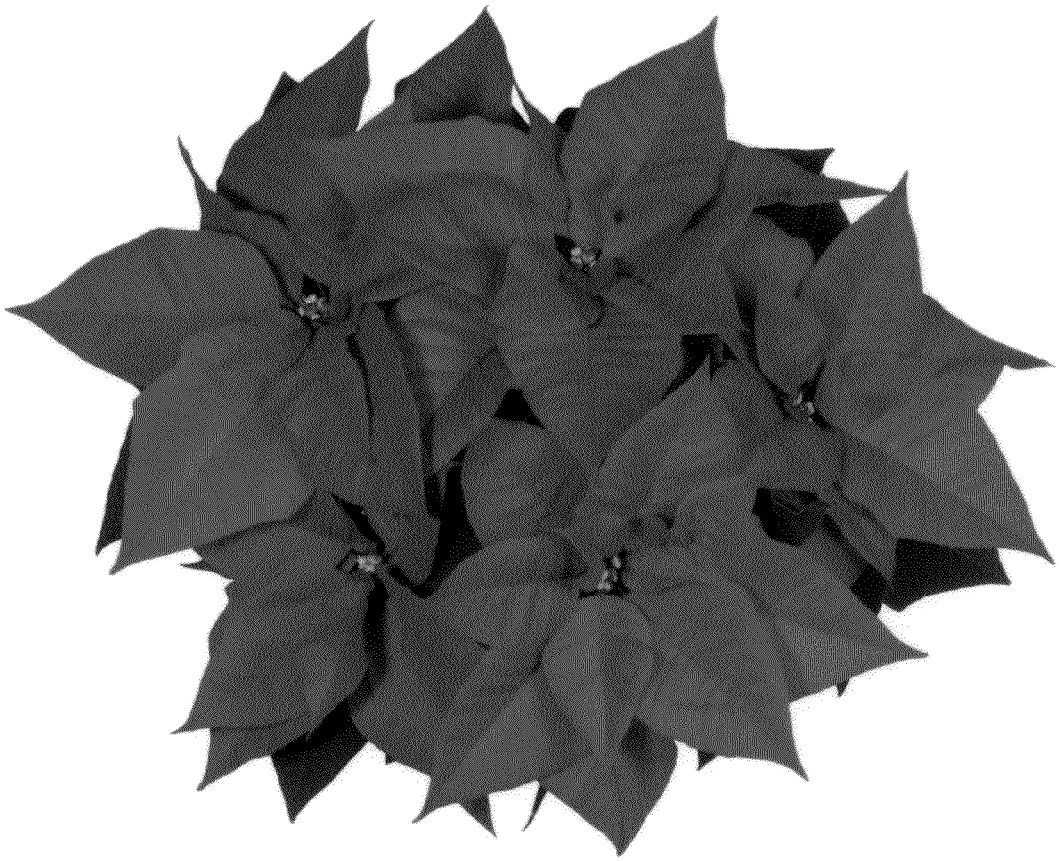

* * * * *